United States Patent [19]
Van Heugten

[11] Patent Number: 5,312,376
[45] Date of Patent: May 17, 1994

[54] CATHETER WITH CLEAR NEEDLE SHAFT

[75] Inventor: Anthony Van Heugten, Tampa, Fla.

[73] Assignee: Critikon, Inc., Tampa, Fla.

[21] Appl. No.: 968,117

[22] Filed: Oct. 29, 1992

[51] Int. Cl.$^5$ .................. A61M 5/32; A61M 5/178
[52] U.S. Cl. ...................... 604/272; 604/168
[58] Field of Search ................. 604/272, 168, 164

[56] References Cited

U.S. PATENT DOCUMENTS

| | | | |
|---|---|---|---|
| 4,240,423 | 12/1980 | Akhavi | 604/272 |
| 4,838,877 | 6/1989 | Massau | 604/272 |
| 5,092,848 | 3/1992 | de Cintins | 604/272 |

FOREIGN PATENT DOCUMENTS

| | | | |
|---|---|---|---|
| 174011 | 3/1986 | European Pat. Off. | 604/272 |
| 403284264 | 12/1991 | Japan | 604/272 |
| 403295566 | 12/1991 | Japan | 604/272 |
| 9007348 | 7/1990 | World Int. Prop. O. | 604/272 |

*Primary Examiner*—John G. Weiss
*Attorney, Agent, or Firm*—Paul A. Coletti

[57] ABSTRACT

This invention relates to a novel needle for expeditiously determining proper insertion of the needle into a patient. A transparent shaft is positioned behind the tip of the needle. Upon insertion of the needle into the vein of a patient, blood is observed in the transparent shaft of the needle. Preferably, the shaft is formed of polyurethane or polycarbonate the needle can be used with an over-the-needle catheter.

12 Claims, 5 Drawing Sheets

CATHETER WITH CLEAR NEEDLE SHAFT

BACKGROUND OF THE INVENTION

1. Field of the Invention

This invention relates to a method and apparatus for improving the determination of proper insertion of a needle.

2. Description of the Related Art

An over-the-needle catheter is a surgical device for insertion into the tissues of a body cavity. A needle and a concentric outer catheter are inserted into the vein of a patient. After insertion, the needle is withdrawn through the emplaced catheter. Fluids can be introduced or removed through the catheter. The problem of quickly determining proper insertion of the needle catheter has persisted in the medical community.

A typical over-the-needle catheter assembly is described in U.S. Pat. No. 4,747,831. In this assembly, a cannula insertion needle projects from the "forward" end of a hollow handle. After the cannula insertion needle is inserted into the patient, the needle is retracted into the handle. A hollow needle is used so that fluids may pass through the needle temporarily while the needle is within the patient. It is disclosed that the needle has a sharpened tip and is made of stainless steel.

One conventional solution for determining when the point of the needle is properly in a blood vessel is to use a transparent housing and flash chamber. U.S. Pat. No. 5,000,740 describes conventional use of a catheter assembly by inserting the concentric catheter and needle through the skin of a patient and into a blood vessel. When the point of the needle is properly located in the vessel, a small amount of blood will flow through the needle and into a flash chamber. Since the needle housing and flash chamber are made of a transparent or translucent polymeric materials, the flow of blood is apparent in the flash chamber. After insertion, the needle is retracted from the catheter into the housing.

Prior art catheters have the disadvantage that after insertion of the catheter into the patient the person inserting the catheter must wait until blood flows into the flash chamber to determine whether or not the catheter has been property inserted. However, the flash chamber is at the end of the catheter that is opposite to the end inserted into the patient. Accordingly, the person inserting the catheter must take his eyes away from the insertion site to check for the appearance of blood in the flash chamber. Prior art catheter also have the disadvantage that if the blood pressure of the patient is low, for example, if the patient is an infant or is suffering from a vascular shutdown, blood may not flow into the flash chamber. Without observing blood in the flash chamber, the person inserting the catheter is unable to determine if the catheter has been properly inserted.

Of possible general relevance to the invention are U.S. Pat. Nos.: 4,850,961; 4,964,854; and 5,053,014 which describe assemblies for over-the-needle catheters.

A practical solution to the problem of expeditiously determining proper insertion of an over the needle catheter in a patient is not found in the prior art.

SUMMARY OF THE INVENTION

Briefly described, the invention comprises a needle for a catheter assembly in which the needle has a transparent body portion. Blood can be expeditiously identified in the needle upon proper insertion of the needle into a vein of the patient. Accordingly, correct insertion of the catheter can be quickly determined. The needle also has the advantage that the person inserting the needle into the patient does not have to take his eyes away from the insertion site to determine if the needle has been properly inserted. The present invention can be used to identify proper insertion of the catheter even if the blood pressure of the patient is low.

In accordance with the teachings of the present invention, the body of the needle is preferably formed of a transparent or translucent material. Most preferably, the body of the needle is formed of a clear plastic polymer such as polycarbonate, polyurethane polysulfane and amorphous nylon. A tip is attached to an end of the needle for ease of insertion of the needle into the patient. Preferably, the tip is formed of sharpened metal or plastic.

DETAILED DESCRIPTION OF THE INVENTION

During the course of this description like numbers will be used to identify like elements according to the different figures which illustrate the invention.

Figure 1:
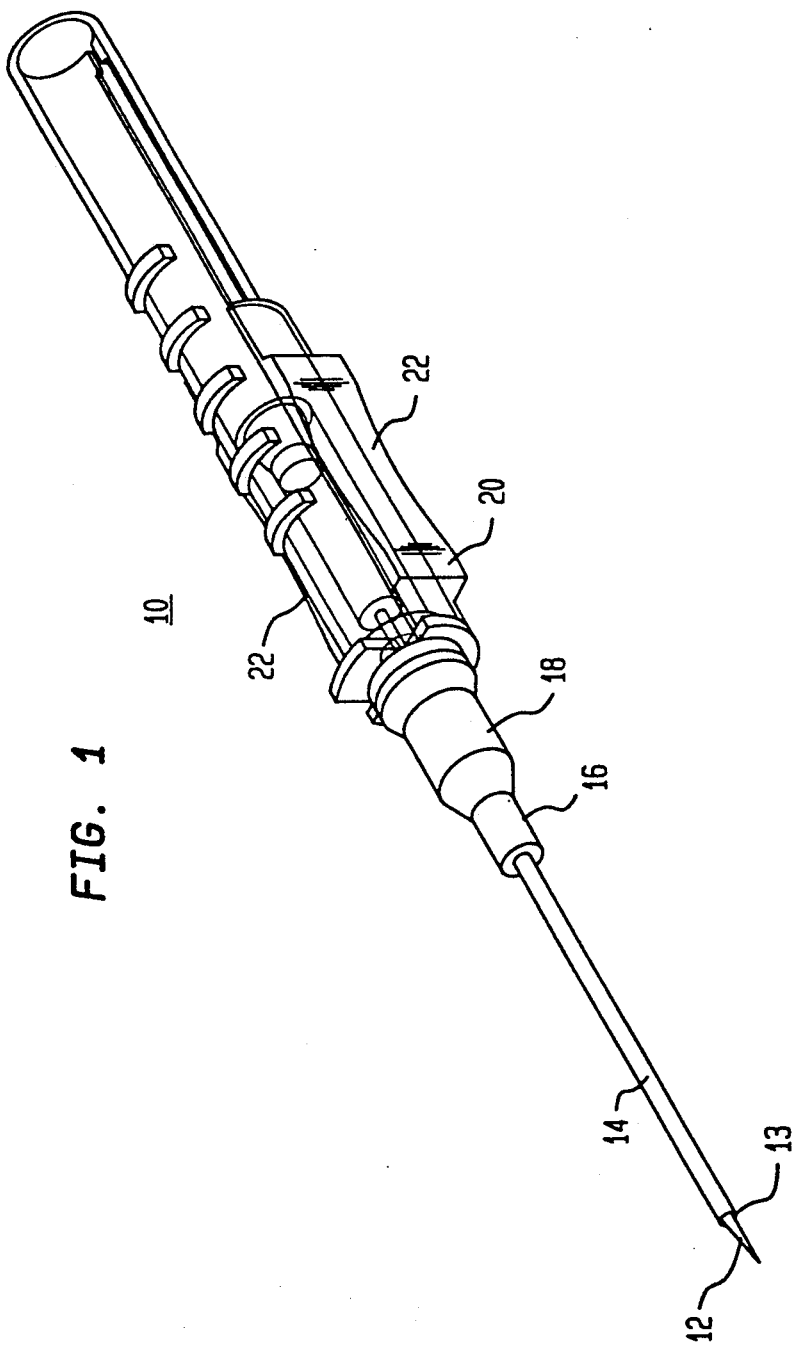
FIG. 1 is a side elevational view of an over-the-needle catheter of the present invention.

FIG. 1 is a side elevational view of catheter assembly 10 in accordance with the principals of the present invention. Catheter assembly 10 includes a needle housing 20 which is semitubular in shape. Molded on the sides are finger grips 22. Catheter 14 extends from catheter hub 16 and is concentric therewith. Catheter 14 can be attached to catheter hub 16 by any means known in the art, including adhesively or mechanically by means of a metal eyelet. Preferably, catheter 14 is a hollow tubular molded polyurethane resin. A larger diameter proximal portion 18 of catheter hub 16 is coupled to needle housing 20.

Figure 2:
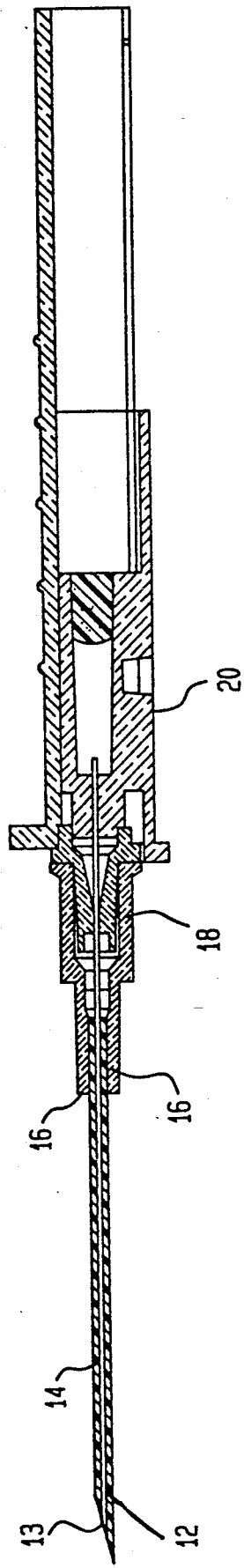
FIG. 2 is a cross-sectional view of the over-the-needle catheter shown in FIG. 1.

As shown in FIG. 2, a tip 13 of needle 12 extends from catheter 14. Tip 13 is preferably formed of sharpened metal for insertion into the vein of the patient. Tip 13 can be attached to needle 12 by vapor depositing the metal onto the needle applying an adhesive between the tip and the needle or by insert molding. In the alternative, tip 13 can be formed of a sharpened plastic material which is integral with needle shaft 15. Tip 13 can be attached to needle 12 by an adhesive or other known means. It will be appreciated that the tip could be formed of other materials known in the art.

Figure 3:
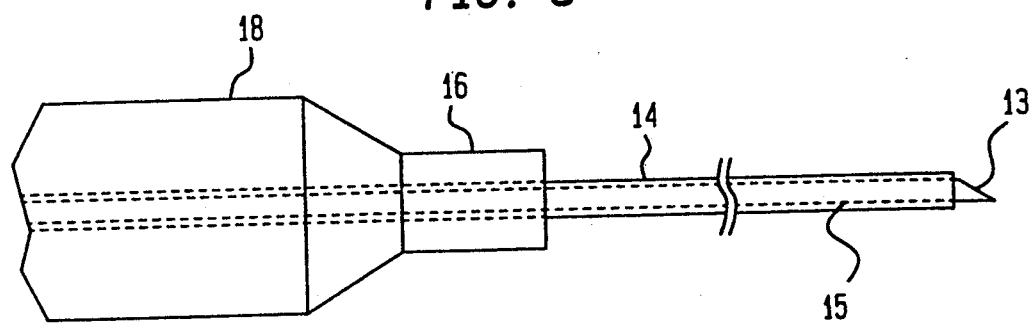
FIG. 3 is a perspective view of the needle of the over-the-needle catheter in accordance with the present invention.
Figure 4:
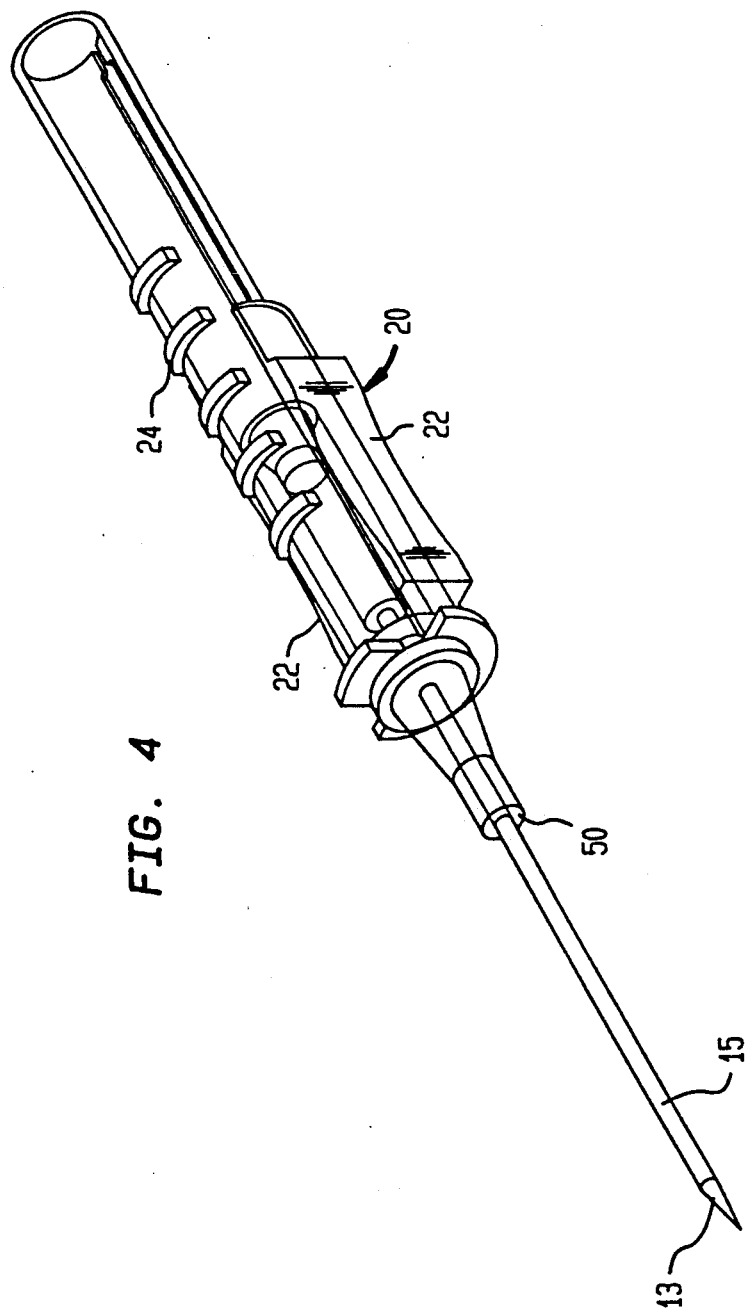
FIG. 4 is a side elevational view of a needle assembly of the present invention.

FIGS. 3 and 4 illustrates needle 12 of the present invention. Needle shaft 15 is positioned behind needle tip 13. Tip 13 is generally defined as about the first 0.10 to 0.50 inches of needle shaft 15. Preferably, needle shaft 15 is formed of a transparent or translucent material. Most preferably, needle shaft 15 is formed of clear plastic polymer. Examples of plastic polymers useful for practice of this invention are polycarbonate, polyurethane, polysulfane and amorphous nylon. It will be appreciated that other transparent or translucent materials could be used in accordance with the teachings of the present invention.

Figure 5:
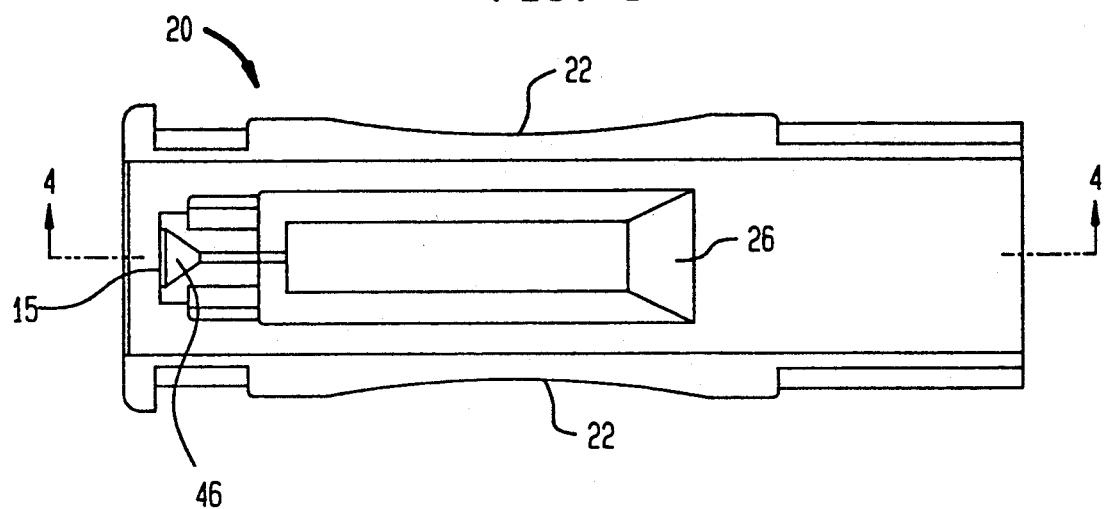
FIG. 5 is a top plan view of the housing and flash chamber of the over-the-needle catheter.
Figure 6:
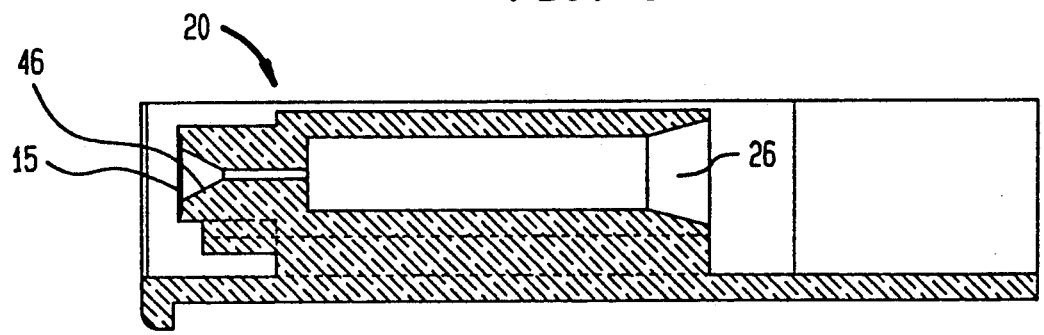
FIG. 6 is a cross-sectional view of the housing and flash chamber of FIG. 5.

FIG. 5 illustrates a perspective view and FIG. 6 illustrates a cross-sectional view of needle 12 attached to flash chamber 26. Preferably, needle 12 has a flared end 46, as shown in FIG. 6. The space around flared end 46 can be filled with adhesive to attach needle 12 to flash chamber 26, as described in U.S. Pat. No. 5,000,740.

Figure 7:
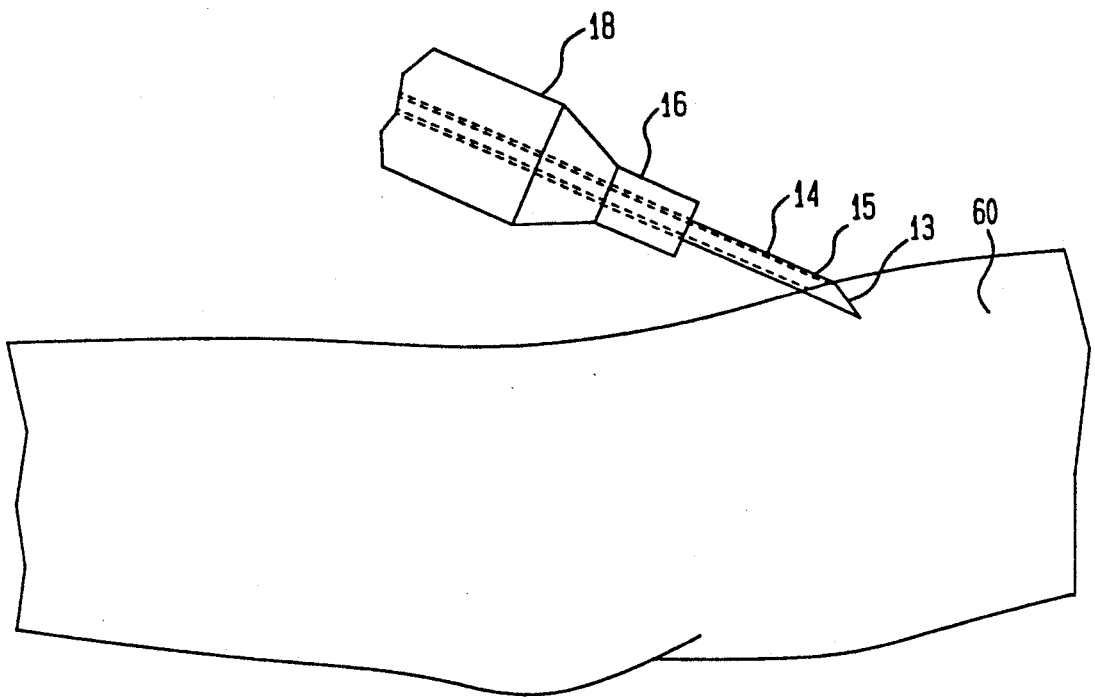
FIG. 7 is a perspective view of the over-the-needle catheter with the needle inserted into the patient.

FIG. 7 illustrates catheter assembly of the present invention after insertion into the vein of patient 60. After proper insertion of tip 13 into the patient's vein, blood flows into needle shaft 15 and can be observed by an observer. Catheter 14 is inserted into the vein when needle 12 is inserted. Blood flows through needle 12 and into flash chamber 26. After insertion, needle 12 can be withdrawn from catheter 14 into catheter hub 16, as described in U.S. Pat. No. 5,000,740.

The present invention has the advantage of reducing the time needed to determine proper insertion of a catheter into the vein of a patient. A transparent needle body provides for expeditiously detecting of blood in the needle. An I.V. can be quickly administered to a patient after expeditiously determining proper insertion of the catheter. The catheter assembly also has the advantage of providing a determination of proper insertion of the catheter in patients having low blood pressure.

While the invention has been described with reference to the preferred embodiment, this description is not intended to be limiting. It will be appreciated by those of ordinary skill in the art that modifications may be made without departing from the spirit and scope of the invention.

I claim:

1. A surgical device for insertion into a body cavity of a patient comprising:
   a hollow needle, said needle having a sharpened metal tip portion and a shaft portion positioned behind said tip portion, said shaft portion being transparent,
   wherein said tip portion pierces said patient to insert said needle into said patient and blood flows from said patient into said shaft portion so that blood can be observed in said shaft portion of said needle.

2. The device according to claim 1 wherein said shaft portion is formed of a clear plastic polymer.

3. The device according to claim 2 wherein said shaft portion is formed of a material selected from the group comprising polyurethane, polycarbonate, polysulfane and amorphous nylon.

4. The device according to claim 3 wherein said tip portion is about 0.1 to about 0.5 inches in length.

5. The device according to claim 4 further comprising:
   a catheter concentric with said needle, said tip portion extending from said catheter.

6. The device according to claim 5 wherein said tip is vapor deposited onto said shaft portion.

7. The device according to claim 5 wherein said tip portion is attached to said transparent portion with an adhesive.

8. The device according to claim 5 wherein said tip portion is attached to said shaft portion by insert molding.

9. A method for determining proper insertion of a surgical device into a patient comprising the steps of:
   inserting a sharpened metal tip of a needle into said patient, said needle having a transparent shaft portion positioned behind said tip, and
   observing blood in said transparent shaft portion upon insertion of said tip into said patient.

10. The method of claim 9 wherein said shaft portion is formed of a clear plastic polymer.

11. The method of claim 10 wherein said shaft portion is formed of a material selected from the group comprising polymers, polyurethane, polycarbonate, polysulfane and amorphous nylon.

12. A surgical device for insertion into a body cavity of a patient comprising:
   a hollow needle, said needle having a sharpened metal tip portion and a shaft portion positioned behind said tip portion, said shaft portion being transparent,
   a catheter concentric with said needle, said tip portion extending from said catheter,
   wherein said tip portion pierces said patient to insert said catheter into said patient and blood flows from said patient into said shaft portion so that blood can be observed in said shaft portion of said needle.

* * * * *